US007778847B2

(12) United States Patent
Kantrowitz

(10) Patent No.: US 7,778,847 B2
(45) Date of Patent: Aug. 17, 2010

(54) SYSTEM FOR MINIMIZING THE COST AND MAXIMIZING THE EFFECTIVENESS OF MONITORING FOR RECURRENCE OF A CONDITION

(75) Inventor: Mark Kantrowitz, Cranberry Township, PA (US)

(73) Assignee: MK Consulting, Inc., Pittsburgh, PA (US)

( * ) Notice: Subject to any disclaimer, the term of this patent is extended or adjusted under 35 U.S.C. 154(b) by 0 days.

(21) Appl. No.: 12/408,495

(22) Filed: Mar. 20, 2009

(65) Prior Publication Data

US 2009/0177491 A1 Jul. 9, 2009

Related U.S. Application Data

(62) Division of application No. 10/818,838, filed on Apr. 6, 2004, now Pat. No. 7,523,043.

(51) Int. Cl.
*G06Q 10/00* (2006.01)
(52) U.S. Cl. ........................................................ 705/2
(58) Field of Classification Search .................. 705/2; 435/6; 726/23
See application file for complete search history.

(56) References Cited

U.S. PATENT DOCUMENTS 6,013,436 A  1/2000  Hui et al.
6,061,657 A  5/2000  Whiting-O'Keefe

OTHER PUBLICATIONS

James S. Hernandez, Cost-Effectiveness of Laboratory Testing, Arch Pathol Lab Med 127:440-445, Apr. 2003.

Giovanni B. Secco, Roberto Fardellii, Daniela Gianquinto, Pierfrancesco Bonfante, Eleonora Baldi, Giambattista Ravera, Lorenzo Derchi, and Romano Ferraris, Efficacy And Cost Of Risk-Adapted Follow-Up In Patients After Colorectal Cancer Surgery: A Prospective, Randomized And Controlled Trial, European Journal of Surgical Oncology (EJSO), 28(4);418-423, Jun. 2002.

Sharon Sharir, Michael A.S. Jewett, Jeremy F.G. Sturgeon, Malcolm Moore, Padraig R. Warde, Charles N. Catton, and Mary K. Gospodarowicz, Progression Detection Of Stage I Nonseminomatous Testis Cancer On Surveillance: Implications For The Follow-Up Protocol, The Journal of Urology, 161(2):472-476, Feb. 1999.

Riad N. Younes, Jefferson L. Gross, and Daniel Deheinzelin, Follow-Up In Lung Cancer: How Often And For What Purporse?, Chest 115(6):1494-9, Jun. 1999.

(Continued)

*Primary Examiner*—Robert W Morgan
*Assistant Examiner*—Valerie Lubin
(74) *Attorney, Agent, or Firm*—The Webb Law Firm

(57) ABSTRACT

A method for determining an optimized surveillance schedule of follow-up diagnostic tests and doctor visits considers the tradeoff between timely detection of relapse and the cost of the diagnostic procedures. A method for generating a surveillance schedule for monitoring a recurrence of a condition includes the steps of (a) scheduling an initial testing date to test for the recurrence of the condition; (b) establishing a threshold, wherein the threshold is the cost associated with a subsequent testing date over the cost per recurrence detected; and (c) scheduling each subsequent testing date to test for the recurrence of the condition when a cumulative risk of recurrence of the condition since the previous testing date exceeds the threshold. A system utilizing this method is also disclosed.

10 Claims, 1 Drawing Sheet

OTHER PUBLICATIONS

Frederic Borie, Jean-Pierre Daures, Bertrand Millat, Margit Folschveiller-Bruggerman, and Brigitte Tretarre, Follow-Up Of Patients With Colorectal Cancer Resected For Cure In The Herault Area: A Medico-Economical Study, Gastroenterol Clin Biol. 25(10):881-4 Oct. 2001.

Olu O. Agboola, Eva Grunfeld, Douglas Coyle, and Gad A. Perry, Costs and Benefits of Routine Follow-Up After Curative Treatment For Endometrial Cancer, Canadian Medical Association Journal 157(7):879-886 Oct. 1, 1997.

S. Ciatto, L. Cionini, and P. Pacini, Cost-Effectiveness Of Chest X-Ray Follow-Up Of Patients Treated For Seminoma Of The Testis, Tumori 72(4):405-8, Aug. 31, 1986. (PubMed Abstract only).

| Month | Probability | Month | Probability | Month | Probability | Month | Probability |
|---|---|---|---|---|---|---|---|
| 1 | 0.18% | 19 | 0.13% | 37 | 0.04% | 55 | 0.02% |
| 2 | 0.22% | 20 | 0.13% | 38 | 0.04% | 56 | 0.02% |
| 3 | 0.24% | 21 | 0.13% | 39 | 0.04% | 57 | 0.02% |
| 4 | 0.25% | 22 | 0.12% | 40 | 0.03% | 58 | 0.02% |
| 5 | 0.26% | 23 | 0.12% | 41 | 0.03% | 59 | 0.02% |
| 6 | 0.24% | 24 | 0.11% | 42 | 0.03% | 60 | 0.02% |
| 7 | 0.21% | 25 | 0.11% | 43 | 0.02% | 61 | 0.02% |
| 8 | 0.19% | 26 | 0.10% | 44 | 0.02% | 62 | 0.02% |
| 9 | 0.18% | 27 | 0.09% | 45 | 0.02% | 63 | 0.02% |
| 10 | 0.17% | 28 | 0.08% | 46 | 0.02% | 64 | 0.02% |
| 11 | 0.17% | 29 | 0.07% | 47 | 0.02% | 65 | 0.02% |
| 12 | 0.16% | 30 | 0.06% | 48 | 0.02% | 66 | 0.02% |
| 13 | 0.16% | 31 | 0.06% | 49 | 0.02% | 67 | 0.02% |
| 14 | 0.15% | 32 | 0.05% | 50 | 0.02% | 68 | 0.02% |
| 15 | 0.15% | 33 | 0.05% | 51 | 0.02% | 69 | 0.02% |
| 16 | 0.15% | 34 | 0.05% | 52 | 0.02% | 70 | 0.02% |
| 17 | 0.14% | 35 | 0.05% | 53 | 0.02% | 71 | 0.02% |
| 18 | 0.14% | 36 | 0.04% | 54 | 0.02% | 72 | 0.02% |

SYSTEM FOR MINIMIZING THE COST AND MAXIMIZING THE EFFECTIVENESS OF MONITORING FOR RECURRENCE OF A CONDITION

CROSS REFERENCE TO RELATED APPLICATIONS

This application is a divisional application of U.S. patent application Ser. No. 10/818,838 filed Apr. 6, 2004.

BACKGROUND OF THE INVENTION

1. Field of the Invention

The present invention is directed to a method and apparatus for minimizing the cost of post-treatment follow-up and diagnostic tests and, more specifically, optimizing the surveillance schedule of follow-up diagnostic tests for cancer.

2. Description of Related Art

Many medical procedures require post-treatment monitoring of the patient's condition. The purpose of this follow-up monitoring, also known as "surveillance", is to detect relapses early enough to allow treatment to resume. In cancer patients, post-surgery surveillance can also be an alternative to radiation therapy and chemotherapy in good-risk patients. Since only about 20% of good-risk patients experience a relapse, surveillance allows 80% of patients to avoid the costs and negative side effects associated with radiation therapy and chemotherapy. Surveillance typically involves a series of regular checkups and diagnostic tests. The diagnostic tests, which can include blood tests, X-rays, CT scans, PET scans and MRIs, can be expensive.

Unfortunately, the surveillance schedule is often ad hoc. For example, the typical surveillance schedule for testicular cancer involves follow-ups every two (2) months during the first ($1^{st}$) year after treatment, every four (4) months during the second ($2^{nd}$) year, every six (6) months during the third ($3^{rd}$) through fifth ($5^{th}$) years, and once a year thereafter. Although this schedule recognizes that most recurrences occur within five (5) years of treatment, and that recurrences are more likely to occur earlier than later, it fails to consider that the risk of relapse drops after each successful diagnostic test and that the risk of relapse decreases within each year. The number of follow-up appointments is also not optimally coordinated with the annual relapse risk.

Similarly, medical professionals recommend that a variety of diagnostic tests be performed on an annual basis after the patient reaches a certain age, as opposed to a schedule that takes age-based incidence rates and probabilities into account. These include mammograms, pap smears, colonoscopy, and prostate tests.

Current methodology for evaluating the tradeoffs between costs and benefits considers only the overall costs, such as the cost per quality of life year saved (QALY). The potential savings from micromanagement of the surveillance schedule is not currently considered.

It is, therefore, desirable to overcome the above problems and others by providing a method for optimizing the surveillance schedule of follow-up diagnostic tests. A more customized surveillance schedule would save significant costs by reducing the number of unnecessary diagnostic tests, while focusing the expenditures where they are most likely to detect disease. This would yield a similar effectiveness at detecting disease but at lower cost. Reducing the number of diagnostic tests will also improve patient compliance with the surveillance schedule, potentially increasing detection rates further. Alternately, the effectiveness could be improved while maintaining the same number of tests and the same cost.

SUMMARY OF THE INVENTION

Accordingly, I have invented a method for determining an optimized surveillance schedule of follow-up diagnostic tests and doctor visits by considering the tradeoff between timely detection of relapse and the cost of the diagnostic procedures. It uses the probability of a recurrence for each month after the end of treatment to maximize the effectiveness in detecting a recurrence (i.e., minimizing the expected delay in detecting a relapse) for a given cost (i.e., for a given number of diagnostic tests). It also uses the probability of recurrence to minimize the cost for a given effectiveness in detecting a recurrence. It recognizes that the cost per detected recurrence increases as the probability of a recurrence decreases, and that the probability of a recurrence decreases as time passes disease-free since the end of treatment. The surveillance schedule should be adjusted to correspond to the risk of a recurrence, considering the amount of time without a recurrence since the end of treatment and the amount of time since the last diagnostic test. The surveillance schedule should also be more intense for high-risk patients and less intense for low-risk patients.

Although various mathematically equivalent methods or derivatives thereof discussed hereinafter may be utilized to determine an optimized surveillance schedule and costs associated therewith, one such exemplary embodiment for determining a subsequent testing date for detection of a disease includes the steps of: a choosing a surveillance schedule, wherein the surveillance schedule includes a plurality of time segments for which a corresponding test is scheduled, wherein the first surveillance schedule has associated therewith a plurality of probabilities representing the probabilities that relapse will be detected in the corresponding plurality of time segments of the surveillance schedule; b.) determining a solution for an equation:

$$\sum_{i=m+1}^{n} P(i) \geq C/T$$

wherein T is a threshold on cost per relapse detected, wherein C is the cost associated with the subsequent testing date, wherein P(i) is the probability that a relapse will be detected in time segment m, wherein n is the time segment of the subsequent testing date; and c.) delaying each subsequent testing date until the cost per detected relapse is below a probability threshold of C/T.

The present invention also notes that a slight delay in detection can yield significant cost savings without compromising patient survival rates. Targeting diagnostic tests when they are most likely to detect recurrence can actually improve the detection rates and reduce the overall delay in detection while cutting costs. In other words, using a more adaptive surveillance schedule will not only reduce costs but also improve detection rates and patient survival. Moreover, by reducing costs, the present invention may make it practical to use diagnostic tests for diseases where the cost/benefit ratio currently precludes the use of such diagnostic tests.

The method may be applied to determine optimized surveillance schedules for conditions including, but not limited to, cancer, heart failure, kidney failure, and emphysema. The forms of cancers may include, but are not limited to, breast cancer, prostate cancer, colon/rectal cancer, leukemia, lymphoma, skin cancer, and lung cancer. Additionally, optimized surveillance schedules may be derived for any condition in which the condition is an event for which an event incidence rate probability may be determined. Such events include, but are not limited to, preventative maintenance tests, quality control tests, and employee monitoring.

Still other desirable features of the invention will become apparent to those of ordinary skill in the art upon reading and understanding the following detailed description.

DETAILED DESCRIPTION OF THE INVENTION

Figure 1:
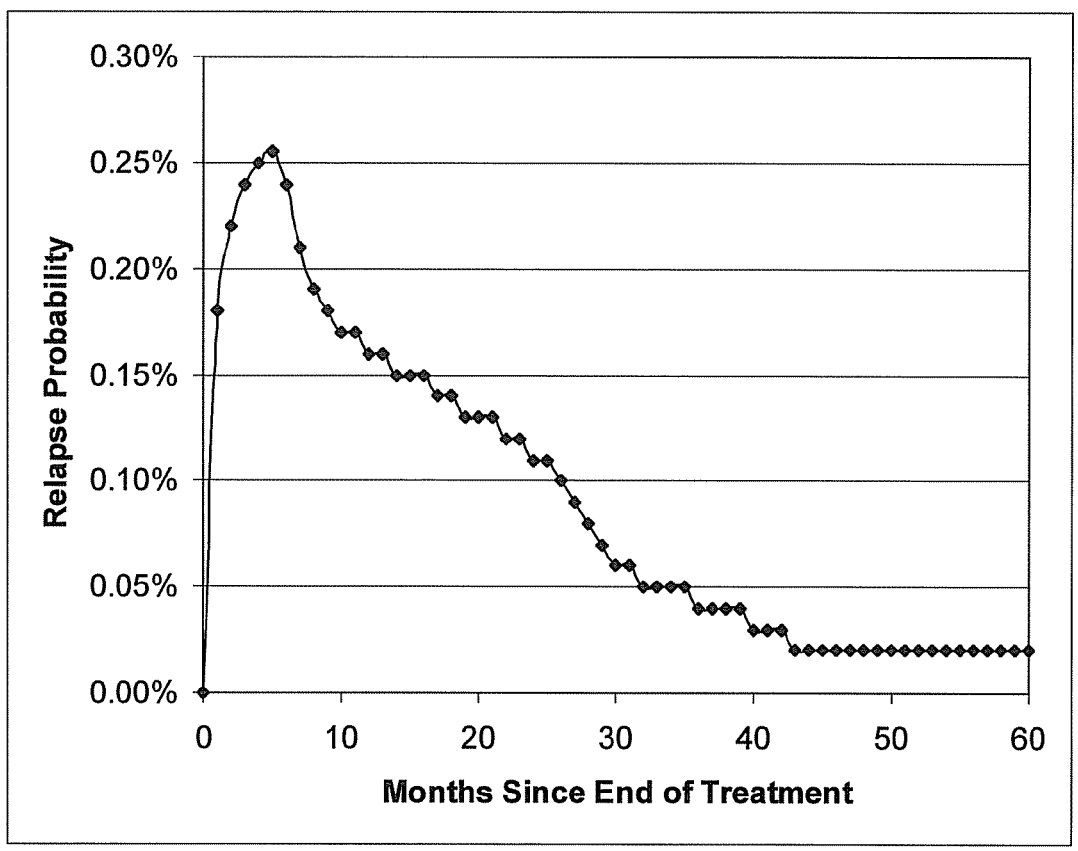
FIG. 1 depicts a table and a graph representative of testicular cancer mortality rates in relation to months since initial treatment of testicular cancer.

It is to be understood that surveillance of a given illness is effective when the following prerequisites are met: 1.) effective therapies exist to permit most patient relapses to be successfully salvaged; 2.) earlier detection of relapses improves the success of salvage therapy and increases the overall survival rate; and 3.) the majority of relapses can be detected by diagnostic tests and not patient symptoms. Testicular cancer satisfies these prerequisites. Thus, the present invention will discuss the method of identifying optimal surveillance schedules in the context of testicular cancer.

The use of physical exams, tumor markers, and CT scans detects approximately two-thirds of relapses, with the remaining third detected by patient symptoms in between routine follow-up appointments. Salvage therapy of testicular cancer is extremely effective, permitting a very high percentage of relapses to be successfully cured. It is to be understood that although other types of cancer and other diseases do not necessarily meet the above prerequisites, eventually, the effectiveness of treatment therapies and diagnostic tests will improve enough that optimizing a follow-up schedule will become important with the other diseases. The method for identifying optimal surveillance schedules involves evaluating the expected delay in detection of a recurrence corresponding to a particular surveillance schedule and the probability of a recurrence for each time segment, such as a month, after the end of treatment. A time segment may encompass a day, a week, a fortnight, a month, a quarter, and a year, or any other unit of time. For preventive maintenance tests, the age-based incidence rates or probability of recurrence are substituted for the number of months since the cessation of treatment. Thus, for any given surveillance schedule, it is possible to arrive at an effectiveness score, namely the expected delay in detection of relapse. The cost corresponds to the number of diagnostic tests required by the surveillance schedule (i.e., the number of follow-up visits and tests).

Since the number of potential surveillance schedules is finite and small, it is possible to exhaustively evaluate the effectiveness of each schedule and pick one of the best schedules. The best schedule can be defined as a schedule that minimizes the number of follow-up tests for a given effectiveness (i.e., minimal cost) or the one that maximizes the effectiveness for a given number of follow-up tests (i.e., maximal effectiveness). The number of possible schedules for the sixty (60) months (five (5) years) after treatment is $2^{60}$ assuming that the number of follow-up tests may range from one (1) test to sixty (60) tests. Practically speaking, the number of follow-up tests can be cut off at fifteen (15), as insurance companies are unlikely to pay for more than fifteen (15) follow-up tests for the typical patient. Currently, the generally accepted surveillance schedule for testicular cancer patients involves fifteen (15) follow-up appointments. That means that the number of possible schedules to evaluate is equal to:

$$\binom{60}{1} + \binom{60}{2} + \binom{60}{3} + \ldots + \binom{60}{14} + \binom{60}{15} = 77,542,088,287,443$$

Since the interval between successive tests should be non-decreasing, the number of distinct possible schedules to evaluate is closer to 2.5 million. A computer program can easily evaluate all of the possible schedules in this set. A further refinement involves decomposing the problem first according to year, in order to determine the number of tests for each year since the end of treatment, and then within the year to assign those tests according to the number of months since the end of treatment.

FIG. 1 shows a table and graph representative of testicular cancer mortality rates in relation to months since initial treatment of the testicular cancer. This data is loosely based on the testicular cancer survival rates in Table XXIV-5, SEER Cancer Statistics Review (1975-2000). It is to be understood that testicular cancer relapse rates seem to be consistent with testicular cancer mortality statistics and, therefore, the data of FIG. 1 may be used for relapse data purposes. Equations may be utilized to compute the expected value of the number of months until a relapse is detected (i.e., expected delay). For example, under the assumption that a test is 100% accurate, if one tests for a relapse every month, the maximum delay in detection of relapse is one (1) month. If a relapse is detected on February 1, but not on January 1, then the relapse became detectable sometime between January 1 and February 1. It is to be understood that testing every month is very costly and, therefore, the surveillance schedule should be optimized based upon the expected delay in detection of a recurrence.

The expected delay in detection of a recurrence can be calculated as follows: Let $M_i$ be the month in which test i occurs. Then let n be the total number of tests. Then $D_i = M_i - M_{i-1}$ is the interval between successive tests. If a relapse is detected in month $M_i$ but not month $M_{i-1}$, then the maximum delay in detection is equal to the interval $D_i$. Let $P(m)$ be the probability that a recurrence will be detected in month m. Then the expected delay in detection for month $M_i$ is the interval $D_i$ multiplied by the probability $P(M_i)$ of detection during test number i and the probability $(1-P(1))(1-P(2)) \ldots (1-P(M_{i-1}))$ that the relapse was not detected during the previous months. The overall expected delay in detection for the entire schedule is equal to the sum of the monthly expected delays, namely:

$$E(M_1 \ldots M_n) = \sum_{i=1}^{n} D_i \cdot P(M_i) \cdot \prod_{j=1}^{i-1} (1 - P(M_j)) \quad (1)$$

$$= \sum_{i=1}^{n} (M_i - M_{i-1}) \cdot P(M_i) \cdot \prod_{j=1}^{M_{i-1}} (1 - P(j))$$

For example, after choosing the surveillance schedule that is to be evaluated, one needs to determine the probability of a relapse in each month of that surveillance schedule. Suppose a patient's first follow-up visit is in Month #4 after the initial treatment, but the relapse actually occurs in Month #2, then the patient will have had a two-month delay in the detection of the relapse. Based upon the relapse data of FIG. 1, one is able to determine what percentage of patients will have had a relapse in Month #1, Month #2, Month #3, etc. Patients who had a relapse in Month #1 would have had a three-month delay in detection, those in Month #2 a two-month delay, those in Month #3 a one-month delay, and those in Month #4 and beyond a O-month delay (for the test in Month #4). Therefore, to compute the expected delay (i.e., expected value of the delay in detection), the probability that a patient is in any of the above month "groups" is multiplied by the delay associated with that month "group", as shown below.

$$ProbabilityOfRelapse(\text{Month\#1}) * 3 \text{ months}$$
$$ProbabilityOfRelapse(\text{Month\#2}) * 2 \text{ months}$$
$$ProbabilityOfRelapse(\text{Month\#3}) * 1 \text{ month}$$
$$ProbabilityOfRelapse(\text{Month\#4}) * 0 \text{ months}$$
$$+ \ldots$$

The following equation represents the equation that results from extending the above summation for each month of the surveillance schedule:

$$E(M_1 \ldots M_n) = \sum_{i=1}^{n} D_i \cdot P(M_i) \qquad (2)$$
$$= \sum_{i=1}^{n} (M_i - M_{i-1}) \cdot P(M_i)$$

More specifically, since the probability of a recurrence in any given month is assumed to be independent of the probability of a recurrence in prior months, then one can omit the product of the probabilities that the recurrence wasn't detected during the previous months, as embodied by equation (2). The independence assumption is reasonable because relapse and mortality statistics are usually reported using the Kaplan-Meier methodology, which incorporates just such an independence assumption.

Equation (1) is similar to equation (2), except that equation (1) looks not just at the probability of relapse, but also factors in the probability that the patient did not relapse in a prior month. After all, if the patient relapsed in a prior month, the patient will have been taken off the surveillance. It is to be understood that both equation (1) and equation (2) may be used to calculate optimal surveillance schedules. The schedules that result will depend on which equation was used to evaluate the expected delay in detection of a recurrence.

If we calculate E for all schedules of length n, we can use it to identify the schedules of length n for which the expected delay is least. Similarly, we can calculate E for all schedules and use it to identify the schedules of a particular expected delay or range of expected delays for which the length n (cost) is least. This allows us to identify the optimal surveillance schedules of a given length n and to compare the expected delay of different surveillance schedules. If we define E(n) to be the minimum expected delay in detection for all schedules of length n, we can use a graph of E(n) or E(n)/n to identify the point of diminishing returns and therefore the best n.

Examining the equations can yield important characteristics of the optimal surveillance schedules. Consider equation (2) in the following circumstances. If the probabilities P(m) are all equal, a surveillance schedule consisting of an even distribution of tests should result. If the probabilities P(m) increase monotonically with increasing m, the surveillance schedule should progress from infrequent to frequent. If the probabilities P(m) decrease monotonically with increasing m, the surveillance schedule should progress from frequent to infrequent.

With equation (1) and equal probabilities P(m), the surveillance schedule should progress from frequent to infrequent, as the individual terms of the sum will be decreasing.

Note, that although the cost is proportional to the number n of follow-up visits in the five (5) year schedule, it is not necessarily equal to n. Cost must take into account that the follow-up schedule ends when a relapse is detected or the patient dies, so a schedule that has more follow-up visits sooner may actually increase costs.

If P(m) is the probability of a relapse or patient death in the interval ending in month m, and C(m) is the cost of the tests in month m, then the following equation is a more precise formulation of the expected costs EC of a particular surveillance schedule:

$$EC(M_1 \ldots M_n) = \sum_{i=1}^{n} C(M_i) \cdot \prod_{j=1}^{M_{ii}} (1 - P(j)) \qquad (3)$$

However, the majority of testicular cancer patients are still alive five (5) years after the end of treatment (95.6%), so any reduction in the total number of necessary follow-up visits will dominate the cost equation. As such, the number n of follow-up visits in a five (5) year schedule represents a reasonable approximation of total costs.

One can minimize the expected delay calculated by equations (1) and (2) by applying a simplifying heuristic. Instead of computing the expected delay for the full schedule, one considers the incremental cost of each successive surveillance appointment per recurrence detected. This method establishes a threshold on the incremental cost per recurrence detected, and sets the next surveillance appointment based on when the probability of a recurrence since the most recent appointment yields a cost per recurrence falling below the threshold. If the cost per recurrence exceeds the threshold, waiting additional months will increase the probability of a recurrence until the incremental cost per recurrence falls below the threshold. Initially, the surveillance will be very frequent because the probability of a recurrence is higher in the early days. The decline in recurrences as time passes since the end of treatment will gradually cause more and more months to pass between follow-up visits. Specifically, let T be the threshold on cost per recurrence detected and C be the cost of a follow-up appointment (or the cost of a particular diagnostic test performed during the follow-up appointment). If the probability of a recurrence in month i is P(i), the last follow-up appointment was in month m and the next follow-up appointment will be in month n, then the cost per recurrence detected is:

$$\text{Cost}(m, n) = C \bigg/ \sum_{i=m+1}^{n} P(i) \qquad (4)$$

If Cost(m,n)>T, increasing n will eventually decrease Cost(m,n) until it falls below the threshold, assuming that the probability of a recurrence after month m is sufficiently high to warrant additional monitoring. If Cost(m,n) will never fall below the threshold, no matter how much n is increased, that signals that month m is the last month of surveillance.

Alternately, we can use the incremental probabilities to trigger a follow-up visit or diagnostic test whenever:

$$\sum_{i=m+1}^{n} P(i) \geq C/T \quad (5)$$

In other words, this equation triggers a new surveillance appointment whenever the cumulative probability of a relapse since the previous diagnostic test exceeds the probability threshold dictated by C/T.

It is to be understood that the threshold on cost per relapse detected may be variable during the iteration of the surveillance schedule derivation when determining each subsequent testing date. Thus, a tolerance or "grace period" may be introduced onto the threshold in situations in which the cost per relapse threshold or threshold on the cumulative risk of a relapse is not constant with time. For example, an insurance company that wants to increase revenue may want to use a lower cost threshold or a higher cumulative risk threshold after the patient has been relapse-free for a certain number of years.

In practical terms, each heuristic establishes a fixed threshold on the cost per relapse detected, regardless of whether the relapse is detected during the first surveillance appointment or during the last surveillance appointment. If one were to test every month, the cost per detected relapse each month would be the cost of the test divided by the probability of a detectable relapse in that month. For example, if it costs $5,000 to perform a CT scan, and only 4% of the patients examined in a certain month have a detectable relapse, it will cost $500,000 to examine 100 patients to detect only 4 relapses. Thus, the cost of each relapse detected is $125,000 (i.e., $5,000/4%). Therefore, if instead of performing such tests every month, one delays the tests according to a schedule, then the cost per relapse detected would be decreased because there would be more relapses detected in each interval for the same number of tests. Although this method may then be used to evaluate the cost associated with any particular surveillance schedule, one can now set a limit on the cost per relapse detected and use that cost to determine the surveillance schedule. For example, one chooses a first surveillance date. If having the first surveillance date as Month #1 yields a cost per relapse above the threshold, then the first surveillance date should be delayed by one (1) or more months until the cost per relapse falls below the threshold. Since the cost of the tests is the same for the first surveillance date, the only variable is the number of relapses detected. That number is simply the sum of the probability of a relapse in each particular month until the surveillance date. This process is then repeated for the next surveillance date, and so forth. If the patient misses a surveillance appointment, one can re-compute the remainder of the surveillance schedule for that particular patient instead of resuming the original schedule, as is currently the common practice. Use of the heuristic allows one to compute an endpoint to the surveillance when the number of likely relapses is so small that no amount of delay will reduce the cost below the threshold. Furthermore, use of the heuristic provides an easier understanding of the present invention for physicians and insurance carriers, as the heuristic places a cost on detecting a relapse and deriving the schedule therefrom.

We can further modify the method to include a minimum number of months that must pass between tests. For example, many oncologists feel that CT scans should not be performed more than once every two months because one (1) month is insufficient time for neoplasms to become detectable. To accommodate this, we add the requirement that:

$$n \geq m+2$$

A requirement that diagnostic tests be performed at least once a year could be implemented by requiring that:

$$n \leq m+12$$

But, it is better to allow tests to become less frequent and eventually end when the cumulative risk of a relapse can no longer be expected to ever exceed the threshold during a normal remaining lifetime.

There may also be a requirement that the surveillance schedule begin no sooner than a certain number of months after the end of treatment. For example, PET scans should be conducted at least six (6) weeks after the end of treatment. Having a PET scan too soon can cause a false positive due to the time required for any remaining cancer cells to die since the previous treatment. Additionally, patients who have recently received immune system boosting drugs to increase their white blood cell counts, might have increased metabolic activity in the bone marrow, thereby causing false negatives elsewhere in the body. Thus, it may be desirable that a certain amount of time pass after the end of treatment prior to initiating the surveillance schedule. To illustrate, consider the relapse statistics of FIG. 1. Using a C/T threshold of 0.4% yields five (5) follow-up tests in the first ($1^{st}$) year (months 2, 4, 6, 8 and 11), four (4) tests in the second ($2^{nd}$) year (months 14, 17, 20 and 24), and one (1) test in each of the third ($3^{rd}$) through fifth ($5^{th}$) years (months 29, 37 and 54). The total number of tests, twelve (12), represents a 20% savings over the standard surveillance schedule. It accomplishes this by eliminating one (1) test in each of the first ($1^{st}$), third ($3^{rd}$), fourth ($4^{th}$) and fifth ($5^{th}$) years, while adding one (1) test in the second ($2^{nd}$) year. Not only does this schedule slightly change the number of tests per year, but it shifts their occurrence within the year to better match the actual risk of relapse.

Increasing the C/T threshold to 0.5% yields follow-up tests in months 3, 5, 8, 11, 15, 19, 23, 29 and 40, (with the next test in month 64), representing a 40% savings. Decreasing the C/T threshold to 0.3% yields follow-up tests in months 2, 4, 6, 8, 10, 12, 14, 16, 19, 22, 25, 29, 35, 45 and 60, yielding no net savings but improving the effectiveness of the surveillance schedule. This change increases the number of tests in the second ($2^{nd}$) and third ($3^{rd}$) years by one and decreases the number of tests in the fourth ($4^{th}$) and fifth ($5^{th}$) years by one, shifting tests to better reflect the risk curve.

The method that has been described herein, may be applied to risk probabilities that are customized on a per-patient basis. For example, if the risk probabilities differ according to patient age, gender, race, disease progression, disease staging, disease morphology, or patient behavior, a more specialized risk table encompassing one or more of these factors, would yield a surveillance schedule that is more appropriate for the patient. The mortality risk for testicular cancer increases with patient age, and testicular cancer occurs more frequently among Caucasian males than African-American or Asian-American males. The risk of relapse also depends on the type and staging of testicular cancer, with seminoma having a lower risk of relapse than non-seminoma, and Stage I having a lower risk of relapse than Stage III. Furthermore, if a patient skips a follow-up test, this method can be used to recalculate the surveillance schedule from that point forward instead of resuming the original schedule.

Even if one lacks information about the risk probabilities, one could improve the schedule by using a surveillance schedule that increases the interval between tests after each test. For example, using an interval of n for the $n^{th}$ test would yield tests in months 2, 4, 7, 11, 16, 22, 29, 37, 46 and 56, for a total of ten (10) tests (33% savings). A related schedule is based on the Fibonacci sequence, yielding tests in months 1, 2, 3, 5, 8, 13, 21, 34 and 55, for a total of nine (9) tests (40% savings).

Furthermore, the optimal surveillance scheduled may be perturbed in various ways including, but not limited to, shifting the subsequent testing date by a month, omitting a month from the surveillance schedule, inserting an additional month between testing dates, and replacing any testing date by the midpoint between two adjacent testing dates (i.e., in a schedule involving months 5, 8, 13, replacing month 8 with the midpoint between months 5 and 13, which is month 9).

For exemplary purposes, the method described herein may be implemented through programming languages, such as PERL or any other suitable programming or scripting language. This implementation includes the requirement that the minimum interval between tests be at least two (2) months and that the threshold range be from 0.2 to 0.74. Thus, the following code:

```
@risk = (0.18, 0.22, 0.24, 0.25, 0.26, 0.24, 0.21, 0.19, 0.18, 0.17,
    0.17, 0.16, 0.16, 0.15, 0.15, 0.15, 0.14, 0.14, 0.13, 0.13,
    0.13, 0.12, 0.12, 0.11, 0.11, 0.10, 0.09, 0.08, 0.07, 0.06,
    0.06, 0.05, 0.05, 0.05, 0.05, 0.04, 0.04, 0.04, 0.04, 0.03,
    0.03, 0.03, 0.02, 0.02, 0.02, 0.02, 0.02, 0.02, 0.02, 0.02,
    0.02, 0.02, 0.02, 0.02, 0.02, 0.02, 0.02, 0.02, 0.02, 0.02);
$max_months = $#risk + 1;
$min_interval = 2;
for each ($threshold = 0.2; $threshold < 0.75; $threshold += 0.01) {
    $cumulative_risk = 0;
    $first_test = 1; $month_counter = 0;
    $schedule = "";
    for each ($month = 0; $month < $max_months; $month++) {
        $cumulative_risk += $risk[$month];
        $month_counter++;
        if ($cumulative_risk >= $threshold &&
            ($first_test || $month_counter >= $min_interval)) {
            if (!$first_test) {
                $schedule .= sprintf ", ";
            } else {
                $first_test = 0;
            }
            $schedule .= sprintf "%d",$month+1;
            $cumulative_risk = 0;
            $month_counter = 0;
        }
    }
    printf "%s\n",$schedule if (!$sawschedule{$schedule});
    $sawschedule{$schedule} = 1;
}
``` may be utilized to generate all possible schedules from the probability distributions in the table of FIG. 1:

2, 4, 6, 8, 10, 12, 14, 16, 18, 20, 22, 24, 26, 29, 33, 38, 46, 57
2, 4, 6, 8, 10, 12, 14, 16, 18, 20, 22, 24, 26, 29, 33, 38, 47, 58
2, 4, 6, 8, 10, 12, 14, 16, 18, 20, 22, 24, 27, 31, 36, 43, 55
2, 4, 6, 8, 10, 12, 14, 16, 18, 20, 22, 25, 28, 32, 37, 46, 58
2, 4, 6, 8, 10, 12, 14, 16, 18, 20, 22, 25, 28, 33, 39, 50
2, 4, 6, 8, 10, 12, 14, 16, 18, 20, 23, 26, 30, 35, 43, 56
2, 4, 6, 8, 10, 12, 14, 16, 18, 21, 24, 27, 31, 37, 47
2, 4, 6, 8, 10, 12, 14, 16, 18, 21, 24, 27, 32, 39, 52
2, 4, 6, 8, 10, 12, 14, 16, 19, 22, 25, 29, 35, 44, 59
2, 4, 6, 8, 10, 12, 14, 16, 19, 22, 25, 29, 35, 45, 60
2, 4, 6, 8, 10, 12, 14, 17, 20, 23, 26, 31, 38, 51
2, 4, 6, 8, 10, 12, 15, 18, 21, 24, 28, 34, 43, 59
2, 4, 6, 8, 10, 12, 15, 18, 21, 24, 28, 34, 44
2, 4, 6, 8, 10, 13, 16, 19, 22, 25, 29, 36, 49
2, 4, 6, 8, 10, 13, 16, 19, 22, 26, 31, 39, 55
2, 4, 6, 8, 11, 14, 17, 20, 23, 27, 33, 43
2, 4, 6, 8, 11, 14, 17, 20, 24, 28, 35, 49
2, 4, 6, 8, 11, 14, 17, 20, 24, 29, 37, 53
2, 4, 6, 8, 11, 14, 17, 20, 24, 29, 37, 54
3, 5, 7, 10, 13, 16, 19, 23, 27, 34, 48
3, 5, 7, 10, 13, 16, 20, 24, 29, 38, 57
3, 5, 7, 10, 13, 16, 20, 24, 29, 38, 58
3, 5, 7, 10, 13, 16, 20, 24, 29, 39, 60
3, 5, 8, 11, 14, 18, 22, 27, 35, 53
3, 5, 8, 11, 15, 19, 23, 28, 38, 60
3, 5, 8, 11, 15, 19, 23, 29, 40
3, 5, 8, 11, 15, 19, 24, 30, 42
3, 6, 9, 13, 17, 21, 26, 35, 55
3, 6, 9, 13, 17, 21, 26, 35, 56
3, 6, 9, 13, 17, 22, 28, 39
3, 6, 9, 13, 17, 22, 28, 40
3, 6, 10, 14, 19, 24, 32, 52
3, 6, 10, 14, 19, 24, 32, 53
3, 6, 10, 14, 19, 25, 35, 60
3, 6, 10, 14, 19, 25, 35
4, 7, 11, 16, 21, 27, 40
4, 7, 11, 16, 21, 28, 43
4, 7, 11, 16, 21, 28, 44
4, 7, 11, 16, 22, 29, 48
4, 7, 11, 16, 22, 30, 51
4, 7, 11, 16, 22, 30, 52
4, 8, 13, 18, 24, 34
4, 8, 13, 18, 24, 35
4, 8, 13, 19, 26, 40

This results in a total of forty-four (44) possible schedules. There are no other possible schedules that can be derived from this particular risk probability distribution. It is important to note how each successive schedule is either a slight perturbation of the previous schedule or a significant jump. The slight perturbations occur toward the end of the schedule, while the jumps occur when there is a slight perturbation earlier in the schedule. The above example illustrates how a slight change early in the schedule, such as a missed appointment, may have a dramatic impact on the remaining schedule, while the schedule is less sensitive later on.

As can be seen, this invention may be of interest to health insurance companies, self-insuring corporations, hospitals, and patients. It can be used to cut costs and improve patient survival rates and quality of life. In particular, it can cut the cost of post-treatment surveillance for cancer patients by as much as 40%, potentially saving health insurance companies millions of dollars a year. The present invention can be used with other types of cancer including, but not limited to, breast cancer, prostate cancer, colon/rectal cancer, leukemia, lymphoma, skin cancer, and lung cancer.

Additionally, the method for determining the optimal surveillance schedule may also be applied to monitor non-health or business related processes or events, such as preventative maintenance schedules for computers and airplanes, quality control, new employee monitoring, and any other process for which event incidence rate probabilities can be identified.

The above invention has been described with reference to the preferred and alternative embodiments. Obvious modifications, combinations, and alterations will occur to others upon reading the preceding detailed description. It is intended that the invention be construed as including all such modifications, combinations, and alterations insofar as they come within the scope of the appended claims or the equivalents thereof.

The invention claimed is:

1. A system for generating a surveillance schedule for monitoring a recurrence of a condition, the system comprising a computer having a non-transitory computer readable medium having stored thereon instructions which, when executed by a processor of the computer, causes the processor to perform the steps of:
    (a) scheduling an initial testing date to test for the recurrence of the condition;
    (b) establishing a threshold, wherein the threshold is the cost associated with a subsequent testing date over the cost per recurrence detected;
    (c) determining that a cumulative risk of recurrence of the condition since the previous testing date exceeds the threshold by:
        (i) defining a cumulative probability of a recurrence of the condition from the test at time segment m to the test at time segment n as CumProb(m,n) by determining a solution for the equation:

$$CumProb(m, n) = \sum_{i=m+1}^{n} P(i)$$

wherein P(i) is the probability that a recurrence will be detected in time segment i;
    wherein m is the time segment of the previous testing date; and
    wherein n is the time segment of the subsequent testing date; and
        (ii) comparing CumProb(m,n) to the threshold established in step (b); and
    (d) scheduling each subsequent testing date to test for the recurrence of the condition based on step (c).

2. A system for generating a surveillance schedule for monitoring a recurrence of a condition, the system comprising a computer having a non-transitory computer readable medium having stored thereon instructions which, when executed by a processor of the computer, causes the processor to perform the steps of:
    (a) scheduling an initial testing date to test for the recurrence of the condition;
    (b) establishing a threshold on a cost per recurrence detected, wherein the cost per recurrence detected is a cost associated with a test for detecting the recurrence of the condition over a cumulative risk of recurrence of the condition since the previous testing date;
    (c) determining that the cost per detected recurrence falls below the threshold by defining a cumulative probability of a recurrence of the condition from the test at time segment m to the test at time segment n as CumProb(m, n) by:
        (i) determining a solution for the equation:

$$CumProb(m, n) = \sum_{i=m+1}^{n} P(i)$$

wherein P(i) is the probability that a recurrence will be detected in time segment i;
    wherein m is the time segment of the previous testing date; and
    wherein n is the time segment of the subsequent testing date; and
        (ii) comparing CumProb(m,n) to the threshold established in step (b); and
    (d) scheduling each subsequent testing date to test for the recurrence of the condition based on step (c).

3. The system of claim 1, wherein the condition is one of (a) cancer, (b) heart failure, (c) kidney failure, and (d) emphysema.

4. The system of claim 1, wherein the condition is any event for which an event incidence rate probability can be determined.

5. The system of claim 4, wherein the event is one of (a) a preventative maintenance test, (b) a quality control test, and (c) employee monitoring.

6. A non-transitory computer readable medium having stored thereon instructions which, when executed by a processor of a computer, causes the processor to generate a surveillance schedule for monitoring a recurrence of a condition by performing the steps of:
    (a) scheduling an initial testing date to test for the recurrence of the condition;
    (b) establishing a threshold, wherein the threshold is the cost associated with a subsequent testing date over the cost per recurrence detected;
    (c) determining that a cumulative risk of recurrence of the condition since the previous testing date exceeds the threshold by:
        (i) defining a cumulative probability of a recurrence of the condition from the test at time segment m to the test at time segment n as CumProb(m,n) by determining a solution for the equation:

$$CumProb(m, n) = \sum_{i=m+1}^{n} P(i)$$

wherein P(i) is the probability that a recurrence will be detected in time segment i;
    wherein m is the time segment of the previous testing date; and
    wherein n is the time segment of the subsequent testing date; and
        (ii) comparing CumProb(m,n) to the threshold established in step (b); and
    (d) scheduling each subsequent testing date to test for the recurrence of the condition based on step (c).

7. A non-transitory computer readable medium having stored thereon instructions which, when executed by a processor of a computer, causes the processor to generate a surveillance schedule for monitoring a recurrence of a condition by performing the steps of:
    (a) scheduling an initial testing date to test for the recurrence of the condition;
    (b) establishing a threshold on a cost per recurrence detected, wherein the cost per recurrence detected is a cost associated with a test for detecting the recurrence of the condition over a cumulative risk of recurrence of the condition since the previous testing date;
    (c) determining that the cost per detected recurrence falls below the threshold by defining a cumulative probability of a recurrence of the condition from the test at time segment m to the test at time segment n as CumProb(m, n) by:

(i) determining a solution for the equation:

$$CumProb(m, n) = \sum_{i=m+1}^{n} P(i)$$

wherein P(i) is the probability that a recurrence will be detected in time segment i;

wherein m is the time segment of the previous testing date; and wherein n is the time segment of the subsequent testing date; and (ii) comparing CumProb(m,n) to the threshold established in step (b); and (d) scheduling each subsequent testing date to test for the recurrence of the condition based on step (c).

8. The non-transitory computer readable medium of claim 6, wherein the condition is one of (a) cancer, (b) heart failure, (c) kidney failure, and (d) emphysema.

9. The non-transitory computer readable medium of claim 6, wherein the condition is any event for which an event incidence rate probability can be determined.

10. The non-transitory computer readable medium of claim 9, wherein the event is one of (a) a preventative maintenance test, (b) a quality control test, and (c) employee monitoring.

* * * * *